United States Patent

Causton et al.

[11] Patent Number: 5,869,600
[45] Date of Patent: Feb. 9, 1999

[54] FILM FORMING ANTIPERSPIRANT POLYMERS

[75] Inventors: Brian E. Causton, Reading; Frederick C. Baines, Dunstable, both of Great Britain

[73] Assignee: The Gillette Company, Boston, Mass.

[21] Appl. No.: 722,591

[22] Filed: Sep. 27, 1996

[51] Int. Cl.$^6$ .................................................. C08G 73/00
[52] U.S. Cl. ........................... 528/422; 525/378; 424/65; 424/47; 424/401; 428/172; 428/423.1
[58] Field of Search ........................... 528/422; 525/378; 424/65, 47, 401; 428/172, 423.1

[56] References Cited

U.S. PATENT DOCUMENTS

| | | | |
|---|---|---|---|
| 3,966,902 | 6/1976 | Chromecek | 424/59 |
| 4,010,252 | 3/1977 | Hewitt | 424/47 |
| 4,057,533 | 11/1977 | Hort et al. | 260/67.5 |
| 4,883,608 | 11/1989 | Trujillo et al. | 252/189 |
| 5,112,886 | 5/1992 | Phalangas | 523/332 |
| 5,209,922 | 5/1993 | Merianos et al. | 424/46 |
| 5,508,024 | 4/1996 | Tranner | 424/59 |

FOREIGN PATENT DOCUMENTS

| | | |
|---|---|---|
| 141269 | 5/1985 | European Pat. Off. . |
| 162388 | 11/1985 | European Pat. Off. . |
| 300490 | 1/1989 | European Pat. Off. . |
| 550969 | 7/1993 | European Pat. Off. . |
| 1485373 | 9/1977 | United Kingdom . |
| 1572259 | 7/1980 | United Kingdom . |

*Primary Examiner*—Duc Truong
*Attorney, Agent, or Firm*—Stephan P. Williams

[57] ABSTRACT

Novel film-forming polymers having a carbon backbone and pendant groups containing quaternised nitrogen atoms, at least one substituent on the quaternised nitrogen being hydrophobic and containing at least 8 carbon atoms, have antiperspirant properties. For use as antiperspirants, they are dissolved or suspended in a non-aqueous carrier with a small amount of water.

84 Claims, No Drawings

FILM FORMING ANTIPERSPIRANT POLYMERS

This is a continuation of pending application Ser. No. PCT/GB95/00800 filed Apr. 6, 1995.

This invention relates to certain film-forming polymers and to their use as antiperspirants.

It has been known for many years to use basic aluminium chloride (ACH) as an antiperspirant material, and products containing it are commonly available for example as aerosols, sticks, roll-ons, gels and creams. Whilst ACH is a very effective antiperspirant, it has some drawbacks and there is concern generally as to the desirability of using aluminium-containing materials for this purpose.

WO 93/24105 describes topical antiperspirant compositions consisting essentially of an effective antiperspirant amount of a non-toxic water-insoluble occlusive film-forming polymer. Among the preferred polymers are alkyl olefinic acid amide/olefinic acid or ester copolymers, alone or in combination with a PVP-linear alpha-olefin copolymer or other water-repellent polymer. These compositions are said to function as antiperspirants by the formation of a water-insoluble occlusive film on the skin, which reduces under-arm perspiration. They are described for use with ACH or alone.

There have been many proposals in the past to apply film-forming polymers to the skin for various purposes. The achievement of good antiperspirancy in this way has, however, proved very difficult. Not only is the quality of antiperspirancy difficult to find, but it is also difficult to overcome the important problem of providing adequate substantivity of the polymer towards the skin so that it remains in place in use.

We have now devised some film-forming polymers which are novel per se and which can provide excellent substantivity when applied topically to the skin, and additionally provide good antiperspirancy.

According to one aspect of the present invention, there is provided a film-forming polymer comprising units of the formulae:

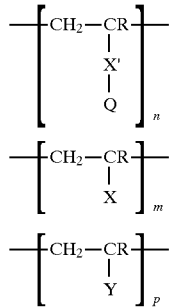

wherein

X is a group which can be directly quaternised by reaction with an amine, or itself comprises a quaternisable nitrogen atom;

X'—Q is quaternised X, where Q is the quaternised nitrogen group and X' may be non-existent;

Q has at least one quaternised nitrogen atom having at least one substituent thereon which is hydrophobic and contains at least 8 carbon atoms;

Y is any atom or group which cannot be directly quaternised and does not comprise a quaternisable nitrogen atom;

R is hydrogen or alkyl (the alkyl preferably being $C_1$ to $C_6$ m and p can each be 0 or an integer;

(n+m+p) is from 20 to 2000, preferably 20 to 1000;

n/(n+m+p) % is from 1% to 100% preferably 25% to 95%; and wherein the polymer can contain two or more different units of formula I, formula II and/or formula III.

These polymers are useful as antiperspirants, and the invention also includes an antiperspirant composition which comprises, as the main or only active antiperspirant ingredient, a film-forming polymer of the invention and a cosmetically acceptable non-aqueous carrier therefor which may be in admixture with a minor amount of water.

In the compositions of the invention, X is a group which either contains a quaternisable nitrogen atom, or which can be directly quaternised by reaction with an amine. The amine(s) can itself be in quaternised form if desired.

The compositions of the invention can contain a small amount (i.e. usually less than 5% by weight) of an aluminium antiperspirant, but in general the presence of aluminium antiperspirants reduces the efficacy of the compositions and we prefer the compositions to be substantially free from aluminium. The compositions can be formulated into aerosol, solid stick, roll-on, gel or cream formulations, for example.

European patent specification no. 0141269 describes certain polyvinyl alcohol polymers having oxylinked pendant quaternary ammonium or tertiary amine groups, as aids in reducing moisture loss when applied to skin as conditioning lotions or ointments in cosmetic and pharmaceutical formulations. In general, moisture loss polymers of this type function by forming a thin film on the surface of the skin. This film reduces transepidermal loss of moisture. However, this is a different effect from the antiperspirancy function of ACH. An antiperspirant functions to stop or significantly reduce the aqueous discharge from sweat ducts, and this is two or more orders of magnitude greater than transepidermal moisture loss. Thus, film-forming polymers known for use in reducing transepidermal loss cannot be expected simultaneously to provide any significant antiperspirant effect. In EP-A-0141269, the polyvinyl alcohol derivatives are used in amounts from 0.5–5% by weight of antiperspirant compositions containing conventional amounts of ACH, one example being 4% of the polymer in a composition containing 57% Al Zr tetrachloro-hydrex-Gly Rezol 36G (Reheis). This is quite different from the compositions of the present invention where amounts of ACH greater than about 5% tend to cause a reduction of antiperspirant efficacy.

Further, the polyvinyl alcohol polymers described in EP-A-0141269 are soluble or dispersible in water so that they will function to reduce transepidermal loss and be compatible with conventional aqueous-based cosmetic and personal care products. In contrast, the polymers used in the present invention are hardly soluble or dispersible in water at all, and require an alcoholic or other non-aqueous solvent carrier. Indeed, dispersions are unstable in the presence of significant amounts of water.

In the polymers of the invention, it is important that the quaternary nitrogen atoms have a hydrophobic substituent of relatively large size, i.e. at least $C_8$. The effect of this hydrophobic substituent is to cause the polymer to change shape in the presence of any water which will be present during use of the polymer as an antiperspirant. It is believed that the change of shape is such as to express the ionic groups and this significantly improves the substantivity towards human skin. The polymers of the invention thus have good substantivity and also show a marked antiperspirant effect.

A preferred substituent for the quaternary nitrogen group is a substituted or unsubstituted hydrocarbyl group containing from 8 to 24 carbon atoms. Possible substituents include, for example, halogen, amino, nitrate, hydroxyl or aryl substituents. More preferably, the hydrocarbyl group is a linear saturated group, most preferably an alkyl group, especially of 12 to 18 carbon atoms, e.g. dodecyl or stearyl. It is to be understood that by "antiperspirant" we mean a substance which when applied to the skin as an antiperspirant reduces wetness by at least 20%. (Federal Register, Oct. 10th 1978 (43 FR 46694) and Federal Register, Aug. 20th 1982 (162 FR 36492).)

Conventionally, antiperspirants are usually formulated as roll-ons, sticks, aerosols, gels or creams. For the manufacture of these formulations, it is preferred in general that the active antiperspirant be in solution. Alternatively, a dispersion can be used provided it is relatively stable. Since the film-forming polymers used in the present invention are generally not soluble in water, they are dissolved or dispersed in a non-aqueous cosmetically acceptable carrier. The amount of film-forming polymer is generally from 1% to 20% by weight, preferably from 6% to 10% by weight. Examples of suitable carriers include alcohols such as ethanol, glycols such as propylene glycol, dipropylene glycol, butylene glycol, triols such as glycerol, propylene carbonate and volatile silicones including, for example, cyclic silicones, linear silicones and low molecular weight dimethicones. Some water can be included provided that the composition remains as a solution or is a stable dispersion. The addition of too much water will destabilise the dispersions. The amount of water which can be tolerated varies from polymer to polymer and with the non-aqueous carrier, and may be as little as 1% up to amounts of 30% or more. It will, however, always be less than the amount of non-aqueous carrier, i.e. it is present in minor amount relative thereto. In any particular case, routine trials will indicate the limits. It is preferred that, in the final formulation, some water be present.

In the case of dispersions of the invention, it is preferred that the disperse phase be from 5 to 10 micrometres in size.

The precise choice of film-forming polymer is not critical. Among the preferred polymers are those wherein, in the units of formula I, X' is an alkylene carbonyl oxy group ($-R_4.CO.O-$) a carbonyl oxyalkylene group ($-CO.O.R_4-$), or an arylene (e.g. $-C_6H_4-$) or aralkylene (e.g. $-C_6H_4-R_4-$) group. Preferably, X' has the formula $-O.CO.CH_2-$(the oxygen being attached to the $-CR$-group) and R is hydrogen or methyl; or X' is a carbonyloxyethylene-oxyethylene group (the carbon being attached to the $-CR$-group) and R is methyl; or X' is a benzyl group (the benzyl $-CH_2$ being attached to Q) and the R is hydrogen. These polymers can be variously derived from, for example, polyvinylalcohol, haloalkyl polystyrenes and polyhydroxyalkyl methacrylates. Halogens can be introduced into hydroxy side-chains using chloroacetate, and the halogen then quaternised.

Other preferred values for X' in the formula I units are:
$-CO.O.R_4-$ $-O.CO.R_4-$
$-CO-$

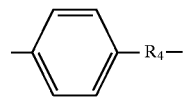

$-CO.O.R_4-O.CO.R_4-$
$-R_4-O.CO.R_4-$
$-CO.NH.CH_2O.COR_4-$
$-CO.O.R_4.OR_4.OCOR_4-$
$-CO.O.R_4.O.R_4-$
wherein each $R_4$ is independently an alkylene group.

Preferably, $R_4$ is an alkylene group of up to 6 carbon atoms, most preferably methylene or ethylene.

Film-forming polymers of the invention with values of X'—Q defined above can be made from many known polymers, including, for example, polyacrylamide, poly (haloalkylacrylate), poly(acryloyl chloride), chloromethylpolystyrene, poly(hydroxyalkyl methacrylate), polysaccharide, poly(allyl alcohol), poly(N-methylol acrylamide), poly(alkylacrylate), poly(alkylmethacrylate) and poly(glycidyl methacrylate). The side chains of these known polymers can be converted to X'—Q side chains of the present invention in various ways, as will be clear to those skilled in the art. For example:

(a) the Mannich reaction can be used to quaternise the amido $NH_2$ group of polyacrylamide.

(b) those known polymers with halogen in the side chain can be quaternised directly by reaction with an amine.

(c) those polymers with a hydroxyl (or epoxide) group in the side chain can be converted to the chloroacetate (or an equivalent halocarboxylate) derivative which can then be quaternised.

(d) those polymers with a carboxyl ester group can be transesterified with, for example, a glycol and then treated as in (c). These procedures are merely examples.

The polymers of the invention can also, of course, be made from known polymers which have at least one quaternisable nitrogen atom present in a side chain. Such known polymers include, for example, polyvinyl pyridine, polyvinyl imidazoline and polyvinyl imidazole. Polymers of the invention include:

(i) those which contain formula I units of formula

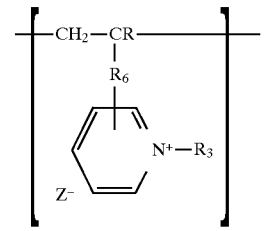

wherein R is hydrogen or an alkyl group, $R_6$ is a single bond or an alkylene group, $R_3$ is hydrophobic and contains at least 8 carbon atoms, and $Z^-$ is an anion.

(ii) those wherein, in the units of formula I, X'—Q is selected from

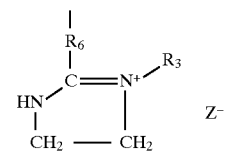

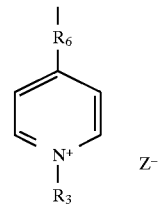

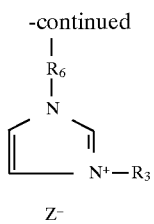

wherein $R_6$ is a single bond or an alkylene group, $R_3$ is hydrophobic and contains at least 8 carbon atoms, and $Z^-$ is an anion.

Among the preferred polymers of the invention are those which comprise units of formula II wherein X is selected from —Hal; —$R_4$Hal; —O.CO.$R_4$.Hal
CO.O.$R_4$.Hal; —CO.Hal;

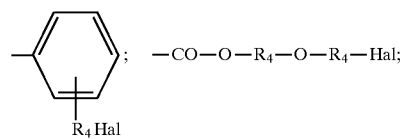

CO.NH.O.CO.$R_4$Hal;
CO.O.$R_4$.O.CO.$R_4$.Hal;

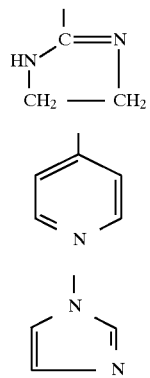

wherein $R_4$ is an alkylene group, and Hal is a halogen. preferably chlorine or bromine.

Preferably, $R_4$ contains from 1 to 6 carbon atoms and is most preferably methylene or ethylene.

In the polymers of the invention, m and p can each independently be zero. Normally, neither m nor p will be zero. When p is not zero, preferred units of formula III include those wherein Y is selected from

—H; —OH; —CONH$_2$; —CO.O.$R_4$.OH;
—$R_4$OH; —CONHR$_4$OH;

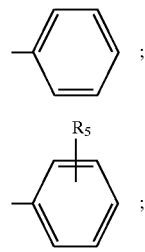

—CO.O.$R_5$; —CO.O.$R_4$.O.$R_4$.OH;

wherein $R_4$ is an alkylene group and $R_5$ is an alkyl group.

Preferably, $R_4$ and $R_5$ will both contain from 1 to 6 carbon atoms, and most preferably $R_4$ is methylene or ethylene.

In the quaternised polymers of the invention, the quaternary nitrogen atoms have one long chain substituent i.e. one substituent having 8 or more, preferably 8 to 25, carbon atoms. Any hydrocarbyl group having from 8 or more carbon atoms can be used. Among the preferred such substituents are $C_{12}$ (dodecyl), $C_{16}$ (hexadecyl) and $C_{18}$ (stearyl) but other substituents may be employed, for example alkylaryl radicals. The preferred $R_1$ and $R_2$ substituents are hydrocarbyl, eg. alkyl groups, having from 1 to 8 carbon atoms. Methyl groups are preferred, but they may themselves carry substituents as desired. Among the possible substituents on the hydrocarbyl groups are halide, amino, nitro, hydroxyl or aryl, for example.

However, regardless of which particular values for the three substituents on the nitrogen are chosen, it is important that together they have a hydrophobicity to promote the substantivity of the polymer as previously described. The substantivity to skin can be impaired if the substituents are so bulky as to cause steric hindrance to the quaternary ammonium ion. Generally, two of the groups will be small relative to the main hydrophobic group of at least 8 carbon atoms.

The quaternised nitrogen atoms may be attached directly to the polymeric backbone but usually instead are attached to a side chain extending from the backbone. In order to promote the formation and stability of the quaternary ammonium groups, the side chain will preferably include some electron withdrawing atoms or groups. Thus, as described above, the side chains can be formed from halocarboxylates, eg. haloacetates, by substituting the quaternised nitrogen at the halogen position. Other halogenated side chains may also be employed to make the quaternised compounds, for example p-chloromethylphenyl units.

The side chain can also be a tertiary aromatic amine, for example 2-pyridyl or 4-pyridyl, or an aliphatic amine, for example dialkylaminoethyl ester and the quaternary formed by using haloalkyls.

The side chain can be any alcohol or ester, the quaternary being added either by the use of base or Lewis acid catalysis of a ring opening addition by a quaternised epoxy or transesterification of a trialkyl oxy-ammonium halide catalysed by a transition metal catalyst.

The nature of the carbon chain backbone of the polymer is not critical provided that it does not contain substituents antagonistic to the intended use of the polyquat. One highly preferred material is polyvinyl alcohol to which side chains can be attached via the pendant OH groups.

In the film-forming polymers of the invention, Q is preferably selected from:

(a) —N$^+$R$_1$R$_2$R$_3$Z, where $R_1$ and $R_2$ are the same or different and are each a $C_1$ to $C_8$ substituted or unsubstituted hydrocarbyl group, $R_3$ is a $C_8$ to $C_{25}$ substituted or unsubstituted hydrocarbyl group, and $Z^-$ is an anion;

(b)

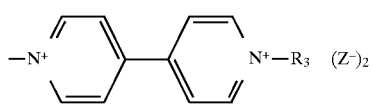

where $R_3$ and each $Z^-$ are independently as defined in (a) above;

(c)

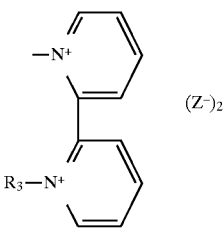

where $R_3$ and each $Z^-$ are independently as defined in (a) above;

(d)

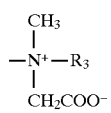

where $R_3$ is as defined in (a) above;

(e)

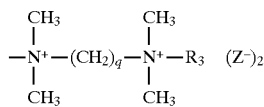

where $R_3$ and each $Z^-$ are independently as defined in (a) above and q is from 2 to 10.

Preferably, $R_1$ and $R_2$ are both alkyl groups. $R_3$ is preferably a linear saturated hydrocarbyl group, preferably $C_{12}$ to $C_{18}$. In the above formulae for Q, and in all occurrences in the specification and claims, $Z^-$ is preferably a halide ion, most preferably chlorine or bromine.

In the diquaternary (e) above, q is preferably 2,3 or 4.

The film-forming polymers used in the present invention can have a very high antiperspirant efficacy. (Efficacy was measured using a standard forearm sweat reduction test and the standard FDA axilla sweat reduction test (Federal Register Aug. 20th 1982 (162 FR 36492.) For example, we have found that a concentration as low as 3% by weight in an aqueous alcohol (30% water) dispersion can be more efficacious than a conventional 20% ACH solution. The efficacy does vary among the polymers. In general, the efficacy increases with increasing chain length of the quaternary nitrogen substituents. Efficacy also tends to increase with increasing water-content of the compositions.

In the quaternised polymers of the invention, it is not essential that every side chain (or group pendant from the main backbone chain) be quaternised. With increasing quaternisation, efficacy tends to rise but very useful and adequate antiperspirancy can be achieved with relatively low quaternisation. Quaternisation can be as low as 1%, but we prefer from about 25% up to 95% or more, and more preferably at least 75%, most especially at least 85%.

The quaternised polymeric materials can be made in a variety of ways as previously described, depending on their precise constitution. Usually, however, a polymeric material with a suitably reactive side chain is reacted with a tertiary amine. For example, poly(vinylchloroacetate) can be reacted with stearyldimethylamine to make the antiperspirant polyquat stearyldimethylamine quaternised poly(vinylchloroacetate). The poly(vinylchloroacetate) can be made by reacting polyvinyl alcohol with chloroacetyl chloride. Those skilled in the art will know of these types of reactions and no further teaching in connection therewith will be given herein.

As stated above, the antiperspirant efficacy of the polyquats is improved by the presence of water. It is preferred, therefore, to use them in formulations where water can be present. Accordingly, we prefer to use them in roll-ons, creams, gels and stick formulations, rather than in aerosols.

The molecular weights of the polymers of the invention can vary widely, but we prefer to use polymers in which (m+n+p) is from 20 to 2000 units, most preferably 200 to 1000 units. In the case of a 25% degree of substitution, 25% of the units in the polymer will be of formula I above. At very high degrees of substitution e.g. 95%, virtually all the polymer units are those of formula I.

The polymers can contain two or more different formula I groups in the same polymer, i.e. mixed polyquats. These polymers are usually made by using two different amines in the quaternisation procedure. They are especially useful in providing a bactericidal effect.

The polymers of the invention can be homopolymers or copolymers made from two or more monomers. It can be advantageous to use copolymers in order to provide more closely the qualities desired in the film-forming polymer. For example, poly(vinylalcohol) polymers can be made softer by copolymerising the vinyl alcohol with ethylene. In the resulting polymers of the invention, the units derived from the ethylene are formula III units in which Y is hydrogen.

In order to make a conventional antiperspirant formulation using the film-forming antiperspirant polymers of this invention, a composition of the invention is mixed with other components of the formulation. The various ways in which this is done will be clear to those skilled in the art. For example, sticks can be formed from a soap gel, a wax, or a dibenzylidine sorbitol product. No detailed description thereof will be given.

In order that the invention may be more fully understood, the following Examples are given by way of illustration only.

EXAMPLE 1

Preparation of chloroacetate derivatives of hydroxy polymers

To the appropriate hydroxy polymer (0.1 mol) were added chloroacetyl chloride (0.3 mol) and water (a few drops). The heterogeneous mixture obtained was stirred at room temperature under anhydrous conditions for 4 h. The viscous homogeneous mixture formed was diluted with ethyl acetate. The polymer was precipitated into an excess of ethanol, filtered and dried under vacuum to give a light brown powder. Yield 75%.

The reaction was performed on poly(vinylalcohol) samples of molecular weight 9,000, 14,000, 22,000 and 49,000, with degrees of polymerisation (DP) of (approximately) 200, 300, 500 and 1100, respectively, and degrees of hydrolysis of 98.4%, 88% and 80%, respectively. The degree of hydrolysis indicates the extent of conversion of polyvinylacetate to polyvinylalcohol.)

EXAMPLE 2

Quaternisation of poly(vinylchloroacetate) with stearyl dimethylamine (SDMA)

The SDMA quaternary was prepared by reacting poly(vinylchloroacetate) with stearyl dimethylamine:

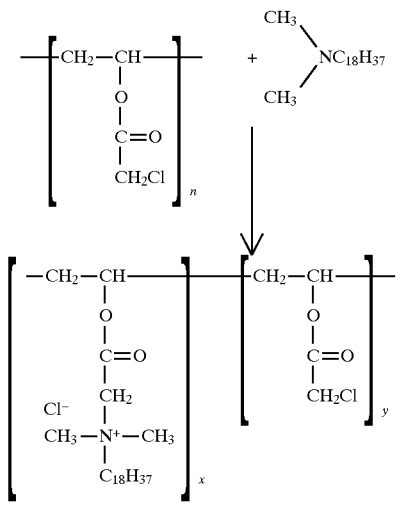

where n=x+y.

The poly(vinylchloroacetate) was derived from 9000 molecular weight poly(vinylalcohol) as described in Example 1. This poly(vinylchloroacetate) (0.1 mol) was dissolved in ethyl acetate (150 ml). To this solution was added the required amount of stearyldimethylamine. This reaction was refluxed for three hours. The quaternised polymer precipitated out. The excess ethyl acetate was decanted off and the product was triturated with ethyl acetate, filtered and dried in a vacuum oven at room temperature. When an equimolar amount of SDMA was added, the substitution was about 88% by nitrogen analysis. Elemental analysis indicated 88% quaternisation.

The ratio of poly(vinylchloroacetate) to SDMA was varied as follows: 1:0.5, 1:0.4, 1:0.3, 1:0.2 and 1:0.1 to provide a number of products of varying quaternisation. The same results were obtained when dimethylformamide was used as the solvent in place of ethyl acetate.

|          | Theory (w/w %) | Found (w/w %) |
|----------|----------------|---------------|
| Carbon   | 69.0           | 64.5          |
| Hydrogen | 11.5           | 10.3          |
| Nitrogen | 3.4            | 3.0           |

EXAMPLE 3

Example 2 was repeated but using dodecyldimethylamine instead of stearyl dimethylamine. Similar results were obtained.

EXAMPLE 4

The efficacy of various solutions of the polyquats of Examples 2 and 3 was tested by routine methods and compared to conventional ACH solutions. The results showed that the stearyl quaternary was more efficacious than the dodecyl quaternary, and that efficacy increased with increasing degrees of quaternisation. In general, the efficacy was close to that of ACH. Substantivity to human skin was excellent. The results of the tests were as follows:

Forearm Efficacy of Polyquat Formulations

| Polyvinyl-chloroacetate | Formulation % w/w ||||  Efficacy % |
|---|---|---|---|---|---|
|  | Polymer | Ethanol | Volatile Silicone VS 344 | Water |  |
| SDMA |  |  |  |  |  |
| 1:1 | 8 | 62 | — | 30 | 70.6 |
|  | 5 | 65 | — | 30 | 64.0 |
|  | 3.5 | 66.5 | — | 30 | 54.0 |
|  | 2 | 68 | — | 30 | 17.5 |
|  | 8 | 72 | — | 20 | 47.8 |
|  | 8 | 82 | — | 10 | 39.2 |
|  | 8 | 62 | 30 | — | 45.9 |
| 1:0.5 | 8 | 62 | — | 30 | 55.3 |
| 1:0.25 | 8 | 62 | — | 30 | 43.8 |
| DDMA |  |  |  |  |  |
| 1:1 | 8 | 62 | — | 30 | 56.6 |
| 1:0.25 | 8 | 62 | — | 30 | 16.8 |

The polyvinylchloroacetate is derived from polyvinyl alcohol (DP 320)

Standard FDA Hot Room Efficacy Test

| Polyvinyl-chloroacetate SDMA | Formulation % w/w |||| Efficacy % |
|---|---|---|---|---|---|
|  | Polymer | Ethanol | Volatile Silicone VS 344 | Water |  |
| 1:1 | 8 | 62 | — | 30 | 28.4 |

Polyvinylchloroacetate derived from polyvinylalcohol (88% hydrolysed DP200)

EXAMPLE 5

Quaternisation of the chloroacetate derivative of poly(2-hydroxyethyl methacrylate) with stearyl dimethylamine The chloroacetate derivative of poly(2-hydroxyethyl methacrylate) (0.01 mol) was dissolved in dimethylformamide (100 ml). To the solution was added stearyl dimethyldiamine (0.012 mol) and this was left stirring at 60° C. for 72 h. The polymer was precipitated into an excess of ethyl acetate, triturated with fresh ethyl acetate (twice) and dried under vacuum to give a pale yellow powder. Yield 60%.

Elemental analysis indicated 40% quaternisation.

|          | Theory (w/w %) | Found (w/w %) |
|----------|----------------|---------------|
| Carbon   | 64.8           | 61.2          |
| Hydrogen | 10.6           | 9.5           |
| Nitrogen | 5.4            | 2.2           |

EXAMPLE 6

Quaternisation of poly(4-vinylpyridine) with 1-bromohexadecane

To a viscous solution of poly(4-vinylpyridine), molecular weight 50000, approximate DP 475, (0.02 mol) in methanol (100 ml) was added 1-bromohexadecane (0.04 mol) and this was stirred under reflux for 5 days. The solvent was removed under vacuum. The polymer was purified by repeated dissolution in dichloromethane and precipitation into an excess of cold diethyl ether. The polymer was dried under vacuum to give a light-brown powder. Yield 85%. Halide analysis indicated 97% quaternisation. Analysis for bromine revealed 18.9% (19.5% expected).

EXAMPLE 7

Quaternisation of poly(vinylbenzylchloride) with stearyl dimethylamine

Poly(vinylbenzylchloride), molecular weight 55000, approximate DP 360, (2 g) and stearyl dimethylamine (3.9 g) were added to ethanol (25 ml) and heated under reflux with stirring for 24 h. The reaction mixture was precipitated into acetone (400 ml) and centrifuged. A white powder was recovered and dried under vacuum to constant weight (5 g). Elemental analysis indicated 90% quaternisation.

|  | Theory (w/w %) | Found (w/w %) |
| --- | --- | --- |
| Carbon | 77.4 | 71.8 |
| Hydrogen | 11.6 | 10.6 |
| Chlorine | 7.9 | 7.3 |
| Nitrogen | 3.1 | 2.7 |

EXAMPLE 8

Co-quaternisation of poly(vinylchloroacetate) with stearyl dimethylamine and 4,4'-dipyridyl N-benzyl bromide Firstly, monoquaternisation of 4,4'-dipyridyl with benzyl bromide was effected as follows. Benzyl bromide (0.05 mol) was added dropwise to a solution of 4,4'-dipyridyl (0.065 mol) in dry acetone (100 ml) and the mixture was refluxed for 4 h. The solid formed was filtered and crystallised from diethyl ether:ethanol to give the pure product. Yield 60%.

|  | Theory (w/w %) | Found (w/w %) |
| --- | --- | --- |
| Carbon | 62.2 | 62.1 |
| Hydrogen | 4.9 | 4.7 |
| Nitrogen | 8.5 | 8.5 |

Then, the monoquaternary of 4,4'-dipyridyl ($2 \times 10^{-4}$ mol) was added to a solution of poly(vinylchloroacetate) (0.01 mol) in dimethylformamide (100 ml) and stirred at 50° C. for 24 h. (The poly(vinylchloroacetate) was made by the method of Example 1 from poly(vinylalcohol) of molecular weight 14000, approximate DP 300.) Stearyl dimethylamine ($1 \times 10^{-2}$ mol) was then added and heating and stirring continued for a further 48 h. The precipitate which formed was triturated with ethyl acetate (twice) and dried to give a white powder. Yield 75%.

EXAMPLE 9

Co-quaternisation of poly(vinylchloroacetate) with stearyl dimethylamine and N-octadecyl-N,N,N',N'-tetramethylethylenediamine bromide Firstly, monoquaternisation of N,N,N',N'-tetramethylethylenediamine with 1-bromooctadecane was effected as follows. 1-bromooctadecane (0.03 mol) was added dropwise to a solution of N,N,N',N'-tetramethylethylenediamine (0.04 mol) in ethanol (200 ml). The mixture was refluxed for 24 h and the solvent removed under vacuum to give a waxy material. Yield 70%.

The monoquaternary of N,N,N',N'-tetramethylethylenediamine ($2 \times 10^{-4}$ mol) was added to a solution of poly(vinylchloroacetate) (0.01 mol) in dimethylformamide (100 ml) and stirred at 50° C. for 24 h. (The poly(vinylchloroacetate) was made from poly(vinylalcohol) of molecular weight 14000, approximate DP 300, by the method of Example 1.) Stearyl dimethylamine ($1 \times 10^{-2}$ mol) was then added and heating and stirring continued for a further 48 h. The precipitate which formed was triturated with ethyl acetate (twice) and dried to give a white powder. Yield 75%.

EXAMPLE 10

Quaternisation of poly(vinylalcohol-co-ethylene) with SDMA

Poly(vinylalcohol-co-ethylene) was converted to the chloroacetate derivative by the process of Example 1.

The poly(vinylchloroacetate-co-ethylene) (0.04 mol, ethylene content 27 mol %) was dissolved in dimethylformamide (150 ml). Stearyl dimethyldiamine (0.035 mol) was added and the mixture stirred at 50° C. for 72 h. The solid precipitate which formed was triturated with fresh ethyl acetate (twice) and dried under vacuum to given an off-white powder. Yield 80%.

EXAMPLE 11

Quaternisation of poly(styrene-co-allyl alcohol) with stearyl dimethylamine

Poly(styrene-co-allyl alcohol) molecular weight 1600, DP approximately 20, was converted to the chloroacetate derivative by the process of Example 1.

The poly(styrene-co-allyl chloroacetate) (0.04 mol. styrene content 94 mol %) was dissolved in ethyl acetate (150 ml). Stearyl dimethyldiamine ($3 \times 10^{-3}$ mol) was added and the mixture stirred at 50° C. for 72 h. The solvent was removed under vacuum. The polymer was purified by repeated dissolution in dichloromethane and precipitation into an excess of cold diethyl ether. The polymer was dried under vacuum to give a pale yellow powder. Yield 75%.

EXAMPLE 12

An example of a roll-on of the invention is:

|  | % |
| --- | --- |
| Polyquat (Example 2) | 8.0 |
| Triclosan | 0.3 |
| Water | 1.0 |
| Cyclomethicone DC344 | 30.0 |
| Ethanol | 60.7 |

EXAMPLE 13

An example of a stick product of the invention is:

|  | % |
| --- | --- |
| Polyquat (Example 2) | 8.00 |
| Ethanol | 53.95 |
| Water | 16.45 |
| Stearyl alcohol | 14.00 |
| Castor oil | 3.00 |
| Talc | 2.20 |
| Silica | 1.40 |
| PEG | 1.00 |

EXAMPLE 14

An example of an aerosol of the invention is:

| | % |
|---|---|
| Polyvinylchloroacetate/DMA (1:1) | 4 |
| Ethanol | 74.5 |
| Triethyl citrate | 1.5 |
| CAP 30 | 20 |

We claim:

1. A topical composition for application to the skin comprising 1% to 20% by weight of a film-forming polymer dissolved in a cosmetically acceptable non-aqueous solvent carrier, wherein said film-forming polymer comprises units of the formula:

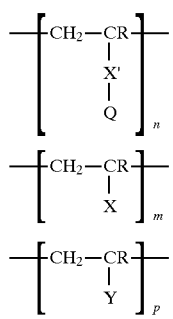

wherein

X is a group which can be directly quaternised by reaction with an amine, or itself comprises a quaternisable nitrogen atom;

X'—Q is quaternised X, where Q is the quaternised nitrogen group and X' may be non-existent;

Q has at least one quaternised nitrogen atom having at least one substituent thereon which is hydrophobic and contains at least 8 carbon atoms;

Y is any atom or group which cannot be directly quaternised and does not itself comprise a quaternisable nitrogen atom;

R is hydrogen or alkyl;

m and p can independently be 0 or an integer;

(n+m+p) is from 20 to 2000;

n/(n+m+p) % is from 25% to 95%;

and wherein the polymer may optionally contain two or more different units of formula I, formula II and/or formula III.

2. The topical composition of claim 1 wherein X'—Q is selected from

—CO—O—$R_4$—Q
—$R_4$—CO—O—Q
—CO—O—$R_4$—O—CO—$R_4$—Q
—CO—O—$R_4$—O—$R_4$—Q
—O—CO—$R_4$—Q
—$C_6H_4$—Q
—$R_4$—O—CO—$R_4$—Q
—CO—O—$R_4$—O—$R_4$—O—CO—$R_4$—Q wherein each $R_4$ is independently an alkylene group of 1 to 6 carbon atoms and Q is selected from (a) —$N^+R_1R_2R_3$  $Z^-$

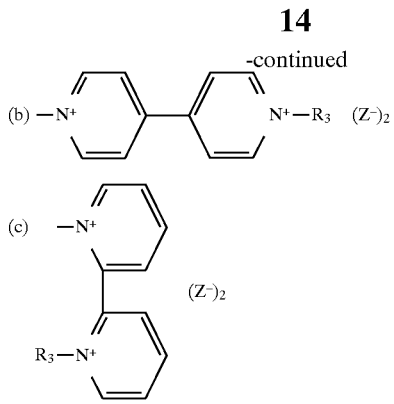

(d) —$\overset{CH_3}{\underset{CH_2COO^-}{N^+}}$—$R_3$ (e) —$\overset{CH_3}{\underset{CH_3}{N^+}}$—$(CH_2)_q$—$\overset{CH_3}{\underset{CH_3}{N^+}}$—$R_3$  $(Z^-)_2$ where $R_1$ and $R_2$ are the same or different and are each a $C_1$ to $C_8$ hydrocarbyl group unsubstituted or substituted with at least one halo, amino, nitro, hydroxyl or aryl group, $R_3$ is a $C_8$ to $C_{25}$ hydrocarbyl group unsubstituted or substituted with at least one halo, amino, nitro, hydroxyl or aryl group, q is an integer from 2 to 10, and $Z^-$ is an anion.

3. The topical composition of claim 1 wherein X'—Q is selected from

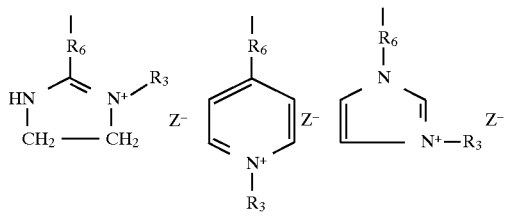

wherein $R_6$ is a single bond or an alkylene group of 1 to 6 carbon atoms, $R_3$ is a $C_8$ to $C_{25}$ hydrocarbyl group unsubstituted or substituted with at least one halo, amino, nitro, hydroxyl or aryl group, and $Z^-$ is an anion.

4. The topical composition of claim 2 or 3 wherein

X is selected from —Hal, —$R_4$—Hal, —O—CO—$R_4$—Hal, —CO—O—$R_4$—Hal, —CO—Hal, —$C_6H_4$—$R_4$—Hal, —CO—O—$R_4$—O—$R_4$—Hal, —CO—NH—O—CO—$R_4$—Hal, —CO—O—$R_4$—O—CO—$R_4$—Hal;

—CO—Q
—$C_6H_4$—$R_4$—Q
—CO—NH—$CH_2$O—CO—$R_4$—Q

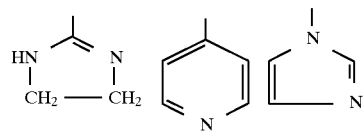

and Y is selected from —H, —OH, —CONH$_2$, —CO—O—R$_4$—OH, —R$_4$—OH, —CO—NH—R$_4$—OH, —C$_6$H$_5$, —C$_6$H$_4$—R$_5$, —CO—O—R$_5$, and —CO—O—R$_4$—O—R$_4$—OH;

wherein R$_4$ is an alkylene group of 1 to 6 carbon atoms, R$_5$ is an alkyl group of 1 to 6 carbon atoms and Hal is a halogen.

5. The topical composition of claim 4 wherein R is H or methyl, R$_1$ and R$_2$ are alkyl, R$_4$ is methylene or ethylene, and Z$^-$ is halide.

6. The topical composition of claim 5 wherein R$_3$ is a linear saturated hydrocarbyl group of 12 to 18 carbon atoms.

7. The topical composition of claim 4 wherein m and p are both integers.

8. The topical composition of claim 7 wherein n+m+p is from 200 to 1000.

9. The topical composition of claim 8 wherein R is H and Y is H.

10. The topical composition of claim 2 wherein X'—Q is —O—CO—CH$_2$—Q and X is —O—CO—CH$_2$—Cl.

11. The topical composition of claim 10 wherein R is H or methyl and Y is H or OH.

12. The topical composition of claim 11 wherein Q is —N$^+$R$_1$R$_2$R$_3$ Z$^-$.

13. The topical composition of claim 12 wherein R$_1$ and R$_2$ are alkyl, R$_3$ is a linear saturated hydrocarbyl group of 12 to 18 carbon atoms, and Z$^-$ is halide.

14. The topical composition of claim 13 wherein m and p are both integers.

15. The topical composition of claim 14 wherein R is H and Y is H.

16. The topical composition of claim 2 wherein X'—Q is —C$_6$H$_4$—CH$_2$—Q and X is —C$_6$H$_4$—CH$_2$—Cl.

17. The topical composition of claim 16 wherein R is H or methyl, Y is H or OH, and Q is —N$^+$R$_1$R$_2$R$_3$ Z$^-$.

18. The topical composition of claim 3 wherein X'—Q is

[pyridinium structure with N$^+$—R$_3$ and Z$^-$]

and X is

[pyridine structure]

wherein R is H and Z$^-$ is halide.

—CO—O—R$_4$—Q          —O—CO—R$_4$—Q          —CO—Q
—R$_4$—CO—O—Q          —C$_6$H$_4$—Q          —C$_6$H$_4$—R$_4$—Q
—CO—O—R$_4$—O—CO—R$_4$—Q  —R$_4$—O—CO—R$_4$—Q     —CO—NH—CH$_2$O—CO—R$_4$—Q
—CO—O—R$_4$—O—R$_4$—Q    —CO—O—R$_4$—O—R$_4$—O—CO—R$_4$—Q

19. The topical composition of claim 4 wherein the non-aqueous solvent carrier comprises ethanol, propylene glycol, butylene glycol, dipropylene glycol, glycerol, propylene carbonate, volatile silicone, or a mixture of two or more of these.

20. The topical composition of claim 19 wherein the non-aqueous solvent carrier comprises ethanol and volatile silicone.

21. The topical composition of claim 19 wherein the non-aqueous solvent carrier additionally comprises up to 30% water, wherein the amount of water is sufficiently low to maintain the composition as a clear solution or stable dispersion.

22. A method of controlling perspiration which comprises applying to an area of skin which perspires a composition comprising 1% to 20% by weight of a film-forming polymer dissolved in a cosmetically acceptable non-aqueous solvent carrier, wherein said film-forming polymer comprises units of the formula:

$$-\left[CH_2-CR\atop{|\atop X'\atop|\atop Q}\right]_n-\quad\text{I}$$

$$-\left[CH_2-CR\atop{|\atop X}\right]_m-\quad\text{II}$$

$$-\left[CH_2-CR\atop{|\atop Y}\right]_p-\quad\text{III}$$

wherein

X is a group which can be directly quaternised by reaction with an amine, or itself comprises a quaternisable nitrogen atom;

X'—Q is quaternised X, where Q is the quaternised nitrogen group and X' may be non-existent;

Q has at least one quaternised nitrogen atom having at least one substituent thereon which is hydrophobic and contains at least 8 carbon atoms;

Y is any atom or group which cannot be directly quaternised and does not itself comprise a quaternisable nitrogen atom;

R is hydrogen or alkyl;

m and p can independently be 0 or an integer;

(n+m+p) is from 20 to 2000;

n/(n+m+p) % is from 25% to 95%;

and wherein the polymer may optionally contain two or more different units of formula I, formula II and/or formula III.

23. The method of claim 22 wherein X'—Q is selected from wherein each R$_4$ is independently an alkylene group of 1 to 6 carbon atoms and Q is selected from (a) —N$^+$R$_1$R$_2$R$_3$ Z$^-$ (b) —N$^+$[biphenyl structure]N$^+$—R$_3$ (Z$^-$)$_2$ -continued (c) 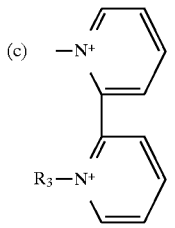

(d) 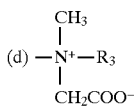

(e) 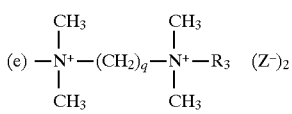

where $R_1$ and $R_2$ are the same or different and are each a $C_1$ to $C_8$ hydrocarbyl group unsubstituted or substituted with at least one halo, amino, nitro, hydroxyl or aryl group, $R_3$ is a $C_8$ to $C_{25}$ hydrocarbyl group unsubstituted or substituted with at least one halo, amino, nitro, hydroxyl or aryl group, q is an integer from 2 to 10, and $Z^-$ is an anion.

24. The method of claim 22 wherein X'—Q is selected from

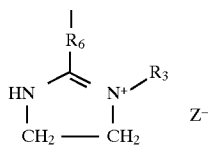

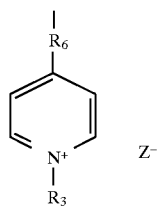

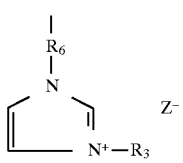

wherein $R_6$ is a single bond or an alkylene group of 1 to 6 carbon atoms, $R_3$ is a $C_8$ to $C_{25}$ hydrocarbyl group unsubstituted or substituted with at least one halo, amino, nitro, hydroxyl or aryl group, and $Z^-$ is an anion.

25. The method of claim 23 or 24 wherein

X is selected from —Hal, —$R_4$—Hal, —O—CO—$R_4$—Hal, —CO—O—$R_4$—Hal, —CO—Hal, —$C_6H_4$—$R_4$—Hal, —CO—O—$R_4$—O—$R_4$—Hal, —CO—NH—O—CO—$R_4$—Hal, —CO—O—$R_4$—O—CO—$R_4$—Hal;

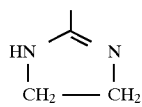

-continued

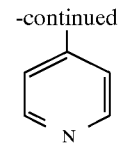

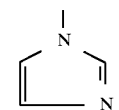

and Y is selected from —H, —OH, —CONH$_2$, —CO—O—$R_4$—OH, —$R_4$—OH, —CO—NH—$R_4$—OH, —$C_6H_5$, —$C_6H_4$—$R_5$, —CO—O—$R_5$, and —CO—O—$R_4$—O—$R_4$—OH;

wherein $R_4$ is an alkylene group of 1 to 6 carbon atoms, $R_5$ is an alkyl group of 1 to 6 carbon atoms and Hal is a halogen.

26. The method of claim 25 wherein R is H or methyl, $R_1$ and $R_2$ are alkyl, $R_4$ is methylene or ethylene, and $Z^-$ is halide.

27. The method of claim 26 wherein $R_3$ is a linear saturated hydrocarbyl group of 12 to 18 carbon atoms.

28. The method of claim 25 wherein m and p are both integers.

29. The method of claim 28 wherein n+m+p is from 200 to 1000.

30. The method of claim 29 wherein R is H and Y is H.

31. The method of claim 23 wherein X'—Q is —O—CO—CH$_2$—Q and X is —O—CO—CH$_2$—Cl.

32. The method of claim 31 wherein R is H or methyl and Y is H or OH.

33. The method of claim 32 wherein Q is —N$^+$R$_1$R$_2$R$_3$ $Z^-$.

34. The method of claim 33 wherein $R_1$ and $R_2$ are alkyl, $R_3$ is a linear saturated hydrocarbyl group of 12 to 18 carbon atoms, and $Z^-$ is halide.

35. The method of claim 34 wherein m and p are both integers.

36. The method of claim 35 wherein R is H and Y is H.

37. The method of claim 23 wherein X'—Q is —$C_6H_4$—CH$_2$—Q and X is —$C_6H_4$—CH$_2$—Cl.

38. The method of claim 37 wherein R is H or methyl, Y is H or OH, and Q is —N$^+$R$_1$R$_2$R$_3$ $Z^-$.

39. The method of claim 24 wherein X'—Q is

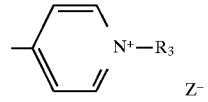

and X is

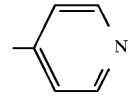

wherein R is H and $Z^-$ is halide.

40. The method of claim 25 wherein the non-aqueous solvent carrier comprises ethanol, propylene glycol, butylene glycol, dipropylene glycol, glycerol, propylene carbonate, volatile silicone, or a mixture of two or more of these.

41. The method of claim 40 wherein the non-aqueous solvent carrier comprises ethanol and volatile silicone.

42. The method of claim 41 wherein the non-aqueous solvent carrier additionally comprises up to 30% water, wherein the amount of water is sufficiently low to maintain the composition as a clear solution or stable dispersion.

43. A topical composition for application to the skin comprising 1% to 20% by weight of a film-forming polymer dissolved in a cosmetically acceptable non-aqueous solvent carrier, wherein said film-forming polymer comprises units of the formula:

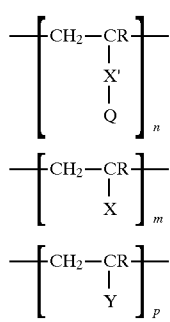

wherein

X is a group which can be directly quaternised by reaction with an amine, or itself comprises a quaternisable nitrogen atom;

X'—Q is quaternised X, where Q is the quaternised nitrogen group and X' may be non-existent;

Q has at least one quaternised nitrogen atom having at least one substituent thereon which is hydrophobic and contains at least 8 carbon atoms;

Y is any atom or group which cannot be directly quaternised and does not itself comprise a quaternisable nitrogen atom;

R is hydrogen or alkyl;

m and p are both integers;

(n+m+p) is from 20 to 2000;

n/(n+m+p) % is 1% or more;

and wherein the polymer may optionally contain two or more different units of formula I, formula II and/or formula III.

44. The topical composition of claim 43 wherein X'—Q is selected from

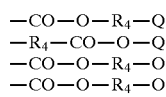 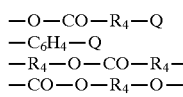 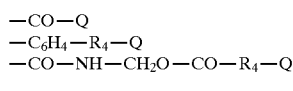

wherein each $R_4$ is independently an alkylene group of 1 to 6 carbon atoms and Q is selected from

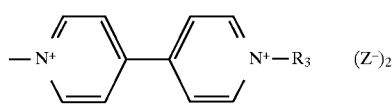

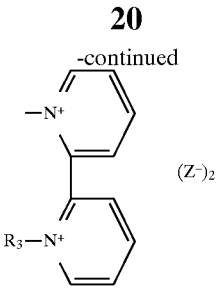

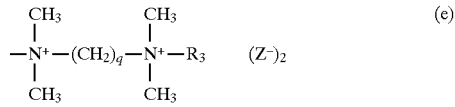

where $R_1$ and $R_2$ are the same or different and are each a $C_1$ to $C_8$ hydrocarbyl group unsubstituted or substituted with at least one halo, amino, nitro, hydroxyl or aryl group, $R_3$ is a $C_8$ to $C_{25}$ hydrocarbyl group unsubstituted or substituted with at least one halo, amino, nitro, hydroxyl or aryl group, q is an integer from 2 to 10, and $Z^-$ is an anion.

45. The topical composition of claim 43 wherein X'—Q is selected from

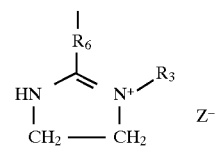

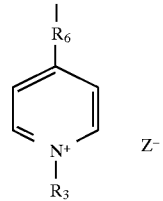

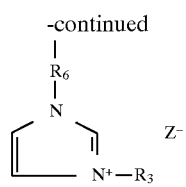

wherein $R_6$ is a single bond or an alkylene group of 1 to 6 carbon atoms, $R_3$ is a $C_8$ to $C_{25}$ hydrocarbyl group unsubstituted or substituted with at least one halo, amino, nitro, hydroxyl or aryl group, and $Z^-$ is an anion.

46. The topical composition of claim 44 or 45 wherein X is selected from —Hal, —R₄—Hal, —O—CO—R₄—Hal, —CO—O—R₄—Hal, —CO—Hal, —C₆H₄—

R₄—Hal, —CO—O—R₄—O—R₄—Hal, —CO—NH—O—CO—R₄—Hal, —CO—O—R₄—O—CO—R₄—Hal;

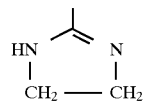

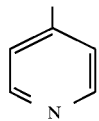

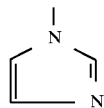

and Y is selected from —H, —OH, —CONH₂, —CO—O—R₄—OH, —R₄—OH, —CO—NH—R₄—OH, —C₆H₅, —C₆H₄—R₅, —CO—O—R₅, and —CO—O—R₄—O—R₄—OH;

wherein R₄ is an alkylene group of 1 to 6 carbon atoms, R₅ is an alkyl group of 1 to 6 carbon atoms and Hal is a halogen.

47. The topical composition of claim 46 wherein R is H or methyl, R₁ and R₂ are alkyl, R₄ is methylene or ethylene, and Z⁻ is halide.

48. The topical composition of claim 47 wherein R₃ is a linear saturated hydrocarbyl group of 12 to 18 carbon atoms.

49. The topical composition of claim 46 wherein n/(n+m+p) % is from 25% to 95%.

50. The topical composition of claim 49 wherein n+m+p is from 200 to 1000.

51. The topical composition of claim 50 wherein R is H and Y is H.

52. The topical composition of claim 44 wherein X'—Q is —O—CO—CH₂—Q and X is —O—CO—CH₂—Cl.

53. The topical composition of claim 52 wherein R is H or methyl and Y is H or OH.

54. The topical composition of claim 53 wherein Q is —N⁺R₁R₂R₃ Z⁻.

55. The topical composition of claim 54 wherein R₁ and R₂ are alkyl, R₃ is a linear saturated hydrocarbyl group of 12 to 18 carbon atoms, and Z⁻ is halide.

56. The topical composition of claim 55 wherein R is H and Y is H.

57. The topical composition of claim 56 wherein n/(n+m+p) % is from 25% to 95%.

58. The topical composition of claim 44 wherein X'—Q is —C₆H₄—CH₂—Q and X is —C₆H₄—CH₂—Cl.

59. The topical composition of claim 58 wherein R is H or methyl, Y is H or OH, and Q is —N⁺R₁R₂R₃ Z⁻.

60. The topical composition of claim 45 wherein X'—Q is

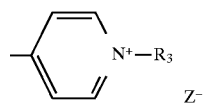

and X is

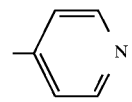

wherein R is H and Z⁻ is halide.

61. The topical composition of claim 46 wherein the non-aqueous solvent carrier comprises ethanol, propylene glycol, butylene glycol, dipropylene glycol, glycerol, propylene carbonate, volatile silicone, or a mixture of two or more of these.

62. The topical composition of claim 61 wherein the non-aqueous solvent carrier comprises ethanol and volatile silicone.

63. The topical composition of claim 61 wherein the non-aqueous solvent carrier additionally comprises up to 30% water, wherein the amount of water is sufficiently low to maintain the composition as a clear solution or stable dispersion.

64. A method of controlling perspiration which comprises applying to an area of skin which perspires a composition comprising 1% to 20% by weight of a film-forming polymer dissolved in a cosmetically acceptable non-aqueous solvent carrier, wherein said film-forming polymer comprises units of the formula:

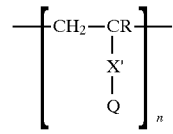

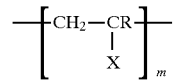

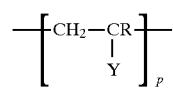

wherein

X is a group which can be directly quaternised by reaction with an amine, or itself comprises a quaternisable nitrogen atom;

X'—Q is quaternised X, where Q is the quaternised nitrogen group and X' may be non-existent;

Q has at least one quaternised nitrogen atom having at least one substituent thereon which is hydrophobic and contains at least 8 carbon atoms;

Y is any atom or group which cannot be directly quaternised and does not itself comprise a quaternisable nitrogen atom;

R is hydrogen or alkyl;

m and p are both integers;

(n+m+p) is from 20 to 2000;

n/(n+m+p) % is 1% or more;

and wherein the polymer may optionally contain two or more different units of formula I, formula II and/or formula III.

65. The method of claim 64 wherein X'—Q is selected from

—CO—O—R₄—Q    —O—CO—R₄—Q    —CO—Q

-continued

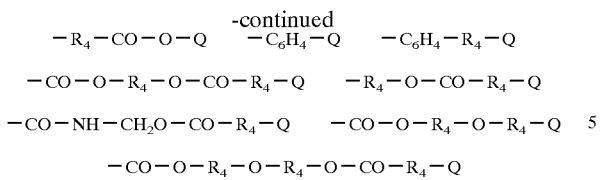

wherein each $R_4$ is independently an alkylene group of 1 to 6 carbon atoms and Q is selected from

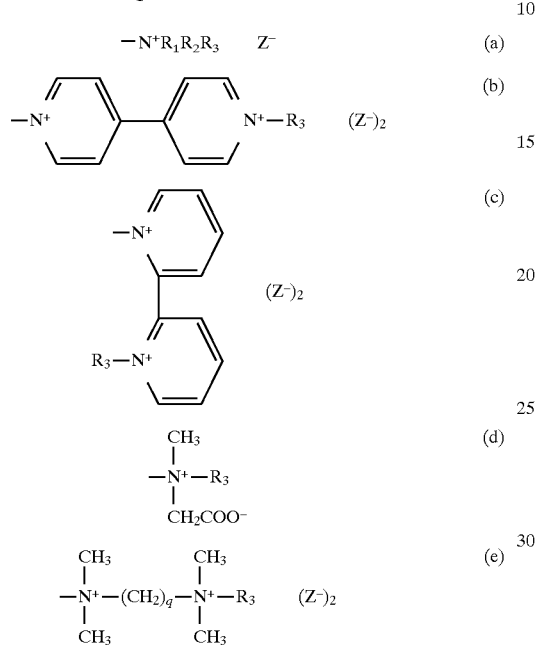

where $R_1$ and $R_2$ are the same or different and are each a $C_1$ to $C_8$ hydrocarbyl group unsubstituted or substituted with at least one halo, amino, nitro, hydroxyl or aryl group, $R_3$ is a $C_8$ to $C_{25}$ hydrocarbyl group unsubstituted or substituted with at least one halo, amino, nitro, hydroxyl or aryl group, q is an integer from 2 to 10, and $Z^-$ is an anion.

66. The method of claim 64 wherein X'—Q is selected from

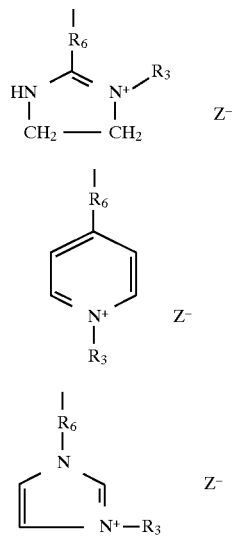

wherein $R_6$ is a single bond or an alkylene group of 1 to 6 carbon atoms, $R_3$ is a $C_8$ to $C_{25}$ hydrocarbyl group unsubstituted or substituted with at least one halo, amino, nitro, hydroxyl or aryl group, and $Z^-$ is an anion.

67. The method of claim 65 or 66 wherein

X is selected from —Hal, —$R_4$—Hal, —O—CO—$R_4$—Hal, —CO—O—$R_4$—Hal, —CO—Hal, —$C_6H_4$—$R_4$—Hal, —CO—O—$R_4$—O—$R_4$—Hal, —CO—NH—O—CO—$R_4$—Hal, —CO—O—$R_4$—O—CO—$R_4$—Hal;

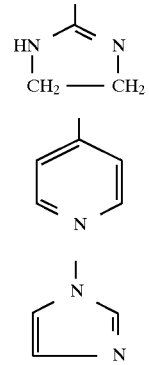

and Y is selected from —H, —OH, —$CONH_2$, —CO—O—$R_4$—OH, —$R_4$—OH, —CO—NH—$R_4$—OH, —$C_6H_5$, —$C_6H_4$—$R_5$, —CO—O—$R_5$, and —CO—O—$R_4$—O—$R_4$—OH;

wherein $R_4$ is an alkylene group of 1 to 6 carbon atoms, $R_5$ is an alkyl group of 1 to 6 carbon atoms and Hal is a halogen.

68. The method of claim 67 wherein R is H or methyl, $R_1$ and $R_2$ are alkyl, $R_4$ is methylene or ethylene, and $Z^-$ is halide.

69. The method of claim 68 wherein $R_3$ is a linear saturated hydrocarbyl group of 12 to 18 carbon atoms.

70. The method of claim 67 wherein n/(n+m+p) % is from 25% to 95%.

71. The method of claim 70 wherein n+m+p is from 200 to 1000.

72. The method of claim 71 wherein R is H and Y is H.

73. The method of claim 65 wherein X'—Q is —O—CO—$CH_2$—Q and X is —O—CO—$CH_2$—Cl.

74. The method of claim 73 wherein R is H or methyl and Y is H or OH.

75. The method of claim 74 wherein Q is —$N^+R_1R_2R_3$ $Z^-$.

76. The method of claim 75 wherein $R_1$ and $R_2$ are alkyl, $R_3$ is a linear saturated hydrocarbyl group of 12 to 18 carbon atoms, and $Z^-$ is halide.

77. The method of claim 76 wherein R is H and Y is H.

78. The method of claim 77 wherein n/(n+m+p) % is from 25% to 95%.

79. The method of claim 65 wherein X'—Q is —$C_6H_4$—$CH_2$—Q and X is —$C_6H_4$—$CH_2$—Cl.

80. The method of claim 79 wherein R is H or methyl, Y is H or OH, and Q is —$N^+R_1R_2R_3$ $Z^-$.

81. The method of claim 66 wherein X'—Q is

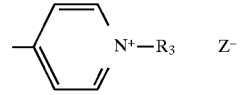

and X is

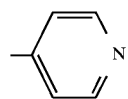

wherein R is H and Z⁻ is halide.

82. The method of claim 67 wherein the non-aqueous solvent carrier comprises ethanol, propylene glycol, butylene glycol, dipropylene glycol, glycerol, propylene carbonate, volatile silicone, or a mixture of two or more of these.

83. The method of claim 82 wherein the non-aqueous solvent carrier comprises ethanol and volatile silicone.

84. The method of claim 82 wherein the non-aqueous solvent carrier additionally comprises up to 30% water, wherein the amount of water is sufficiently low to maintain the composition as a clear solution or stable dispersion.

* * * * *